(12) United States Patent
Dorsey et al.

(10) Patent No.: US 9,486,303 B2
(45) Date of Patent: Nov. 8, 2016

(54) IMPLANTABLE MEDICAL DEVICE RETRIEVAL SYSTEM, APPARATUS, AND METHOD

(71) Applicant: Cook Medical Technologies LLC, Bloomington, IN (US)

(72) Inventors: Michael Dorsey, Sylvania, OH (US); Jacqueline Jaworek, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 50 days.

(21) Appl. No.: 14/204,594

(22) Filed: Mar. 11, 2014

(65) Prior Publication Data

US 2014/0277067 A1  Sep. 18, 2014

Related U.S. Application Data

(60) Provisional application No. 61/783,384, filed on Mar. 14, 2013.

(51) Int. Cl.
*A61M 29/00* (2006.01)
*A61F 2/01* (2006.01)

(52) U.S. Cl.
CPC ............ *A61F 2/01* (2013.01); *A61F 2002/011* (2013.01)

(58) Field of Classification Search
CPC .... A61F 2/013; A61F 2002/011; A61F 2/95; A61F 2/01; A61B 2017/2217; A61B 17/221
USPC ........................................................ 606/200
See application file for complete search history.

(56) References Cited

U.S. PATENT DOCUMENTS

| | | | |
|---|---|---|---|
| 4,793,348 A | | 12/1988 | Palmaz |
| 5,304,122 A | * | 4/1994 | Schwartz et al. ............ 604/509 |
| 5,769,821 A | * | 6/1998 | Abrahamson et al. ....... 604/104 |
| 5,893,869 A | | 4/1999 | Barnhart et al. |
| 5,947,985 A | | 9/1999 | Imran |
| 7,258,696 B2 | | 8/2007 | Rabkin et al. |
| 7,534,252 B2 | | 5/2009 | Sepetka et al. |
| 7,691,110 B2 | | 4/2010 | Secrest et al. |

(Continued)

OTHER PUBLICATIONS

Van Ha et al., "Techniques Used for Difficult Retrievals of the Gunther Tulip Inferior Vena Cava Filter: Experience in 32 Patients," *J Vasc Interv Radio* (2009); 20: pp. 92-99.

(Continued)

*Primary Examiner* — Richard Louis
(74) *Attorney, Agent, or Firm* — Brinks Gilson & Lione

(57) ABSTRACT

A system for retrieving an implantable medical device includes a delivery sheath that houses an inflatable balloon catheter and a retrieval device. The retrieval device includes a first support rod and a second support rod and a helix extending between distal ends of the first support rod and the second support rod. The inflatable balloon catheter is translatable into a position between the implantable medical device and a wall of a patient blood vessel. The balloon is inflated to force the device away from the wall. The helical member of the retrieval device is expanded radially be translating the second support rod distally. The helical member is moved over the balloon catheter and the medical device, where rotation of the first support rod will cause the helical member to radially compress to trap the balloon catheter and medical device therein for subsequent retrieval from the body.

19 Claims, 4 Drawing Sheets

(56) References Cited

U.S. PATENT DOCUMENTS

| | | |
|---|---|---|
| 7,976,562 B2 | 7/2011 | Bressler et al. |
| 8,252,019 B2 | 8/2012 | Fleming, III |
| 2004/0215229 A1* | 10/2004 | Coyle ........................... 606/200 |
| 2006/0184193 A1* | 8/2006 | Lowe et al. .................. 606/200 |
| 2006/0224177 A1* | 10/2006 | Finitsis ........................ 606/200 |
| 2008/0065205 A1* | 3/2008 | Nguyen et al. .............. 623/2.36 |
| 2010/0063534 A1 | 3/2010 | Kugler et al. |
| 2012/0109180 A1 | 5/2012 | Shrivastava |
| 2012/0184987 A1* | 7/2012 | Sirota ........................... 606/200 |

OTHER PUBLICATIONS

Kuo et al., "High-risk Retrieval of Adherent and Chronically Implanted IVC Filters: Techniques for Removal and Management of Thrombotic Complications," *Journal of Vascular and Interventional Radiology*, 20(12); (2009); pp. 1548-1556.

Lynch, F.C., "Balloon-assisted Removal of Tilted Inferior Vena Cava Filters with Embedded Tips," *Journal of Vascular and Interventional Radiology*, 20; (2009); pp. 1210-1214.

Vink et al., "Balloon-Assisted Retrieval of Tilted OptEase IVC Filter," *CardioVascular and Interventional Radiology*, 35(4); (2012); pp. 975-977.

\* cited by examiner

IMPLANTABLE MEDICAL DEVICE RETRIEVAL SYSTEM, APPARATUS, AND METHOD

CROSS-REFERENCE TO RELATED APPLICATIONS

This application claims the benefit under 35 U.S.C. §119 (e) of U.S. Provisional Application No. 61/783,384, filed Mar. 14, 2013, which is hereby incorporated by reference in its entirety.

BACKGROUND

The present invention relates to medical devices. More particularly, the invention relates to a retrieval system for removing an implantable medical device from a patient blood vessel.

Filtering devices that are percutaneously placed in the vena cava have been available for over thirty years. A need for filtering devices arises in trauma patients, orthopedic surgery patients, neurosurgery patients, or in patients having medical conditions requiring bed rest or non-movement. During such medical conditions, the need for filtering devices arises due to the likelihood of thrombosis in the peripheral vasculature of patients wherein thrombi break away from the vessel wall, risking downstream embolism or embolization. Typically, filtering devices are permanent implants, each of which remains implanted in the patient for life, even though the condition or medical problem that required the device has passed. In more recent years, filters have been used or considered in preoperative patients and in patients predisposed to thrombosis which places the patient at risk for pulmonary embolism.

However, there are instances in which retrieval of the filter from the vena cava of a patient is desirable. For example, filtering may no longer be necessary, the filter may interfere with subsequent medical procedures, or the filter may become tilted or oriented in such a way that the filter does not operate as intended. Portions of the filter may become embedded in the vessel wall over time, making retrieval more difficult. While filter retrieval devices are known in the art, improvements can be made to assist in the removal of vena cava filters.

SUMMARY

A system for retrieving a medical device from a blood vessel is provided, the system comprising: a balloon catheter having a proximal end and a distal end and an inflatable balloon portion disposed at the distal end; an elongate retrieval device extending along the balloon catheter, the retrieval device comprising a first elongate support rod having proximal and distal ends, a second elongate support rod having proximal and distal ends, and a helix extending between the distal ends of the first and second support member, wherein the helix extends around at least a portion of the balloon catheter; wherein the elongate retrieval device has a first condition, with the distal end of the second support rod being disposed proximally from the distal ends of the first support rod, and the helix extending between the distal ends has a first width; and wherein the elongate retrieval device has a second condition, with the distal end of the second support rod being disposed distally relative to the first configuration and the helix extending between the distal ends of the first and second support rods has a second width that is greater than the first width.

In another form, an apparatus for retrieving a medical device from a body vessel is provided, the apparatus comprising: an elongate tubular sheath having a proximal end and a distal end and defining lumen extending therebetween; a double lumen catheter extending through the lumen of the sheath, the double lumen catheter having proximal and distal ends, a first lumen, and a second lumen; a balloon catheter extending through the lumen of the sheath alongside the double lumen catheter; a first support rod extending within the first lumen of the double lumen catheter; a second support rod extending within the second lumen of the double lumen catheter; and a helical member at least partially exposed from the double lumen catheter and extending between distal ends of the first and second support rods, wherein the helical member spirals around at least a portion of the balloon catheter.

A method for retrieving an implantable medical device from a patient blood vessel is provided, the method comprising: delivering a sheath having an inflatable balloon catheter and a radially adjustable retrieval device therein to a blood vessel, wherein the radially adjustable retrieval device includes a first support rod, a second support rod, and a helical member extending between distal ends thereof and surrounding a portion of the inflatable balloon catheter; translating the balloon catheter out of the sheath and between an implantable medical device and a wall of the blood vessel; inflating the balloon catheter to force the implantable medical device away from the blood vessel wall; translating the helical member of the radially adjustable retrieval device at least partially over the balloon catheter and the implantable medical device; radially compressing the helical member around the balloon catheter and the implantable medical device; and retracting the retrieval device, the balloon catheter and the implantable medical device.

DETAILED DESCRIPTION

Figure 1:
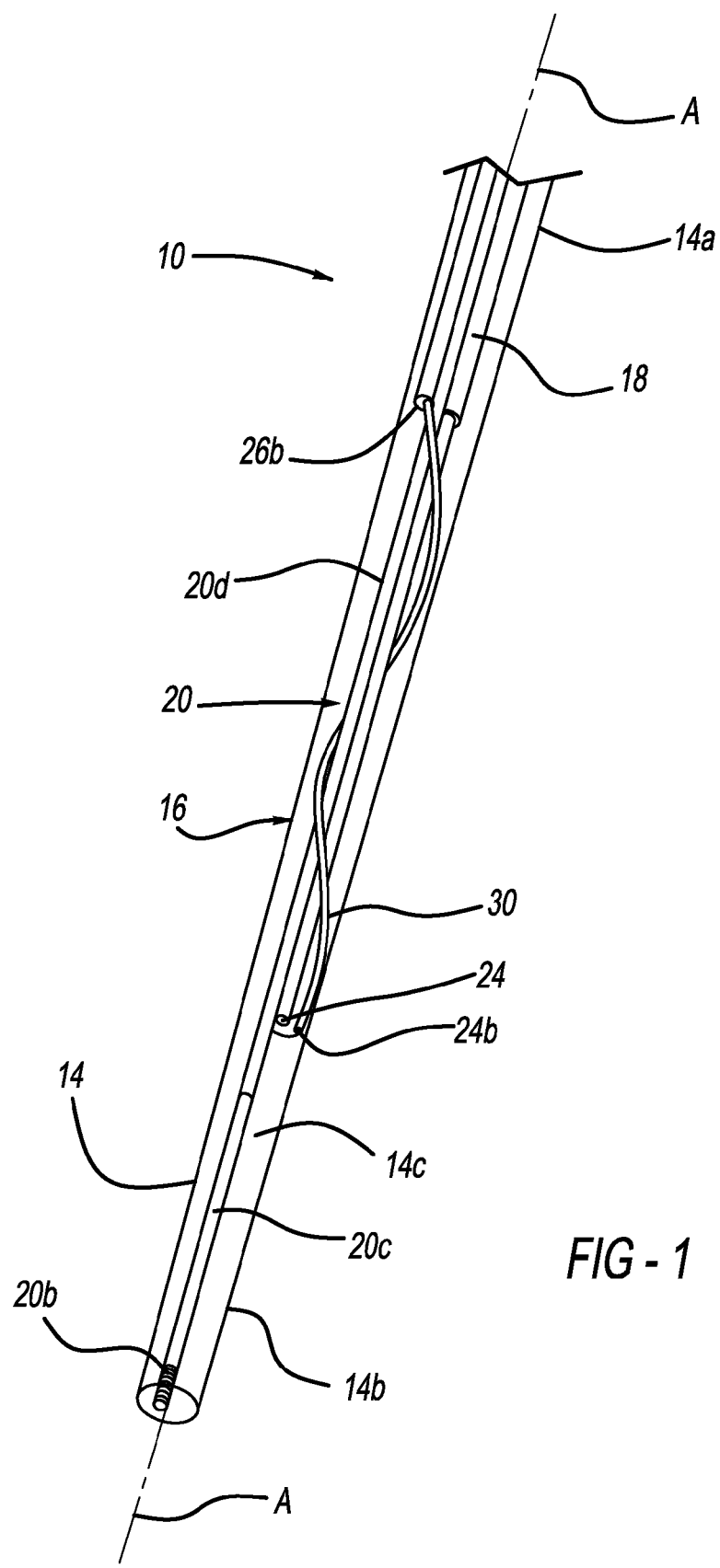
FIG. 1 is an isometric view showing a system for retrieving an implantable medical device from a patient blood vessel, where the system includes a sheath, a retrieval device housed within a catheter, and a balloon catheter, with the system shown in a delivery configuration.

The terms "proximal" and "distal" as used herein are intended to have a reference point relative to the user. Specifically, throughout the specification, the terms "distal" and "distally" shall denote a position, direction, or orientation that is generally away from the user and towards a target site, and the terms "proximal" and "proximally" shall denote a position, direction, or orientation that is generally towards the user and away from a target site. Thus, "proximal" and "distal" directions, portions of a device, or bodily regions, may depend on the point of entry for the procedure (e.g., percutaneously or laparoscopically or endoscopically).

Referring now to the drawings, FIGS. 1-9 illustrate a system 10 for removing a vena cava filter 12 (FIGS. 4-9) from a body vessel in which the filter 12 has been previously delivered to the patient's body. Various types of filters and delivery methods for deploying the filter 12 within the patient's body are known in the art, as will not be discussed in detail. In addition to the ability to remove the vena cava filter 12, the system 10 can also be used to remove and retrieve other implantable medical devices that are barbed, anchored, or hooked into a body vessel or tissue including, but not limited to, bariatric stents, bariatric sleeves, and embolization coils. The device 10 can be used in a similar manner to that described herein in relation to removing the filter 12, where the system 10 can be used to remove the medical device from its implantation in the vessel wall or tissue and be captured and retracted.

Figure 2:
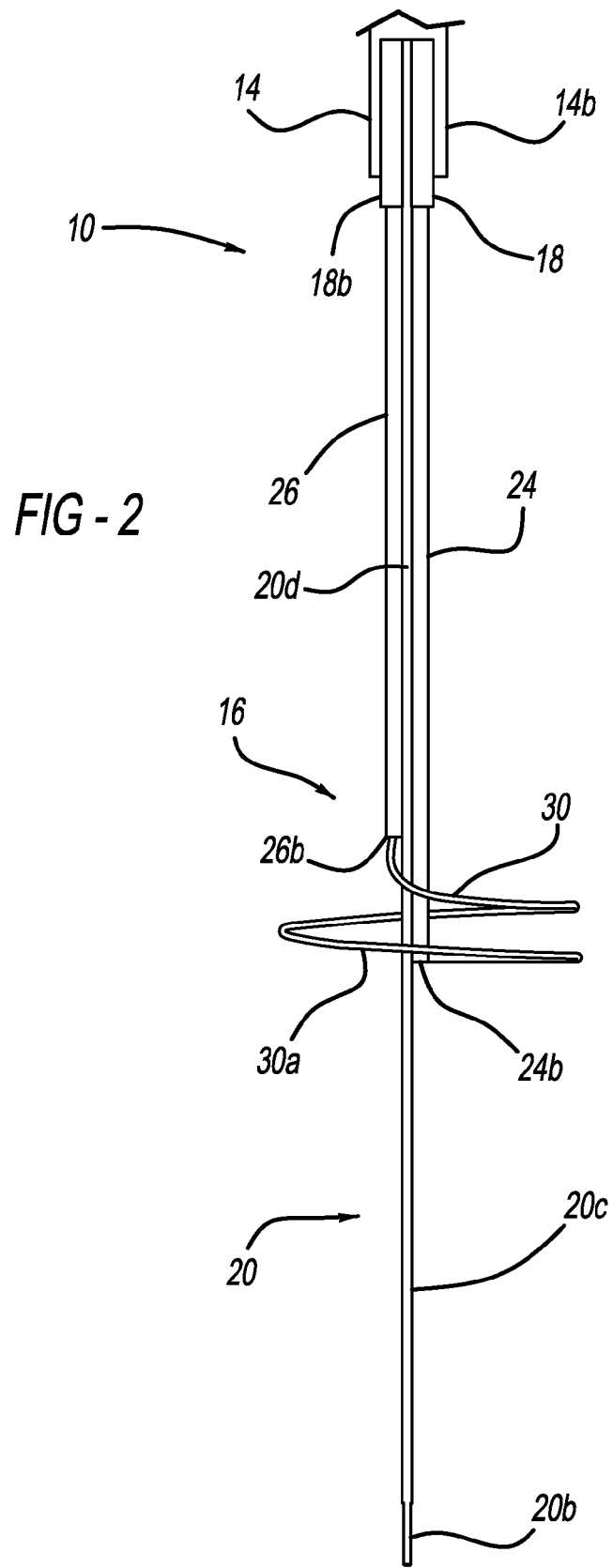
FIG. 2 is a top view of the system in an exposed configuration, showing first and second support rods of the retrieval device and a helical member extending between distal ends thereof, with the support rods positioned to radially expand the helical member.

With reference to FIGS. 1 and 2, the system 10 includes a sheath 14, a retrieval device or retriever 16, a double lumen catheter 18, and a balloon catheter 20. The sheath 14 houses the retriever 16, the double lumen catheter 18, and the balloon catheter 20. More particularly, the retriever 16 is disposed at least partially within the double lumen catheter 18, which will be further described below. The retriever 16, double lumen catheter 18, and balloon catheter 20 are each moveable relative to each other in a longitudinal direction to allow for selected delivery from and retrieval to the sheath 14.

The sheath 14 can be a typical delivery or retrieval sheath known in the art, having a proximal end 14a and distal end 14b and defining a lumen 14c extending therebetween. The proximal end 14a of the sheath 14 can be coupled to a control mechanism or handle 22 for manipulating the various components of the system 10, further described below. The sheath 14 also defines a longitudinal axis A extending generally along the center of the lumen 14c. The sheath 14 can be sized to conform to the needs of the user. For example, the sheath 14 can be made long enough to extend sufficiently into the patient's body to retrieve the filter 12, and can be made wide enough to accommodate the sizing of the double lumen catheter 18, the balloon catheter 20, and the retriever 16.

Figures 3, 3A:
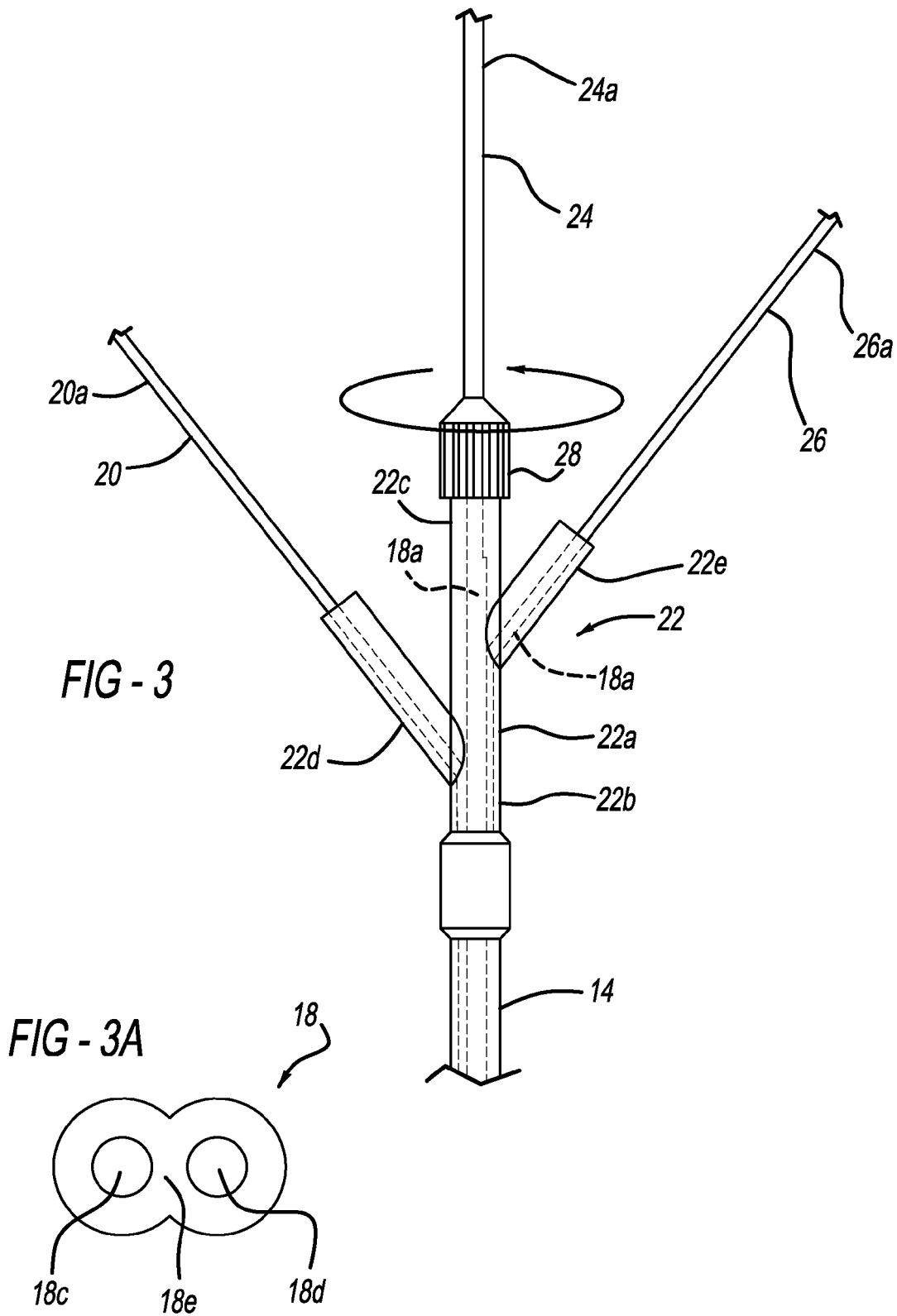
FIG. 3 is a bottom view of a handle of the system, showing the sheath coupled thereto and portions of the balloon catheter and the support rods extending therefrom.
FIG. 3A is a schematic cross-sectional view of the catheter showing a pair of lumens.

With reference to FIGS. 2 and 3, the retriever 16 includes a first support rod 24 and a second support rod 26. The support rods 24 and 26 each have proximal ends 24a, 26a and distal ends 24b, 26b. The first support rod proximal end 24a can be coupled to a spinner 28 mounted to the handle 22. The spinner 28 is capable of spinning 360 degrees to rotate the first support rod 24 along its length. The retriever 16 further includes a helical member or helix 30 that extends between the distal ends 24b and 26b of the support rods 24, 26. In the preferred form, the first support rod 24 is thicker, having a larger diameter than the second support rod 26. In this manner, the first support rod 24 can be referred to as the thick support rod 24, and the second support rod can be referred to as the thin support rod 26. Of course, it will be appreciated that the first support rod 24 could be thinner than the second support rod 26 in some cases.

As will be further described below, the thick support rod 24 can be rotated by the spinner 28, with the thin support rod 26 remaining rotationally fixed (or rotating a lesser amount or in the opposite rotational direction) to adjust the radial shape and size of the helix 30, such that the helix 30 can be made to radially expand and contract in response to rotation of thick support rod 24. Furthermore, the helix 30 can be made to extend and compress longitudinally in response to longitudinal translation of the thin support rod 26 relative to the thick support rod 24. This relative translation of the support rods 24, 26 can be seen in FIGS. 1 and 2, where FIG. 1 shows the helix 30 generally elongated and FIG. 2 shows the helix 30 compressed longitudinally.

With reference to FIGS. 1-3A, the double lumen catheter 18 includes a proximal end 18a and a distal end 18b, with the proximal end 18a coupled to the handle 22 in a manner known in the art, and extending longitudinally through the sheath lumen 14c. The double lumen catheter 18 defines a first a lumen 18c and a second lumen 18d. The first and second lumens 18b, 18c are separated by a webbing 18e extending along the length of the double lumen catheter 18. While the lumens 18s and 18d are preferably separate and distinct, in another form, the lumens 18b and 18c could be combined into a single lumen (not shown) with the support rods 24, 26 extending within the single lumen together.

The retriever 16 is housed at least partially within the double lumen catheter 18. More specifically, the thick support rod 24 extends through the first lumen 18c, with the thin support rod 26 extending through the second lumen 18d. Of course, the opposite arrangement could also be used. In the case of a single lumen, the thick and thin support rods 24, 26 would extend through the single lumen.

With reference to FIGS. 1-3, the system further includes the balloon catheter 20, which includes a proximal end 20a and a distal end 20b. The proximal end 20a is coupled to the handle 22 in a manner known in the art. More specifically, the balloon catheter 20 includes an inflatable balloon portion 20c at the distal end 20b that is coupled to a tubular body portion 20d that extends proximally from the balloon portion 20c. As known in the art, the body portion 20d defines a lumen therethrough (not shown) that is in fluid communication with a cavity (not shown) of the balloon portion 20c. Inflation fluid can be delivered or retrieved through the lumen to inflate and deflate the balloon portion 20c in a manner known in the art. The body portion 20d can extend through the handle for connection to a fluid source (not shown). It will be appreciated that other arrangements and configurations of balloon catheters known in the art could also be used, and the above description of the balloon catheter 20 is general in nature.

The balloon catheter 20 extends through the lumen 14c of the sheath 14, alongside the double lumen catheter 18 that houses the retriever 16. These components can be adjusted relative to each other by manipulating their proximal ends, which are coupled to the handle 22.

With reference to FIG. 3, the handle 22 includes a tubular longitudinal portion 22a having a distal end 22b coupled to the sheath 14 and a proximal end 22c that is coupled to the spinner 28. The handle 22 further includes first and second tubular branch portions 22d, 22e that extend from the longitudinal portion 22. The branches 22d, 22e are in fluid communication with the lumen 22 longitudinal portion 22a. In one form, the first branch portion 22d extends from the longitudinal portion 22a at a location distal to the second branch portion 22e, such that the second branch portion 22e is disposed closer to the proximal end 22c of the longitudinal portion 22a and the spinner 28. However, the opposite could also be true, as well as the branch portions 22d, 22e being disposed at approximately the same longitudinal position along the longitudinal portion 22a. The first and second branch portions 22d, 22e can extend from diametrically opposite sides of the longitudinal portion 22a, or could extend from generally radially adjacent positions on the longitudinal portion 22a.

In a preferred form, the balloon catheter 20 extends out of the first branch portion 22d for being coupled to the inflation fluid source. The balloon catheter 20 can be pushed and pulled through the first branch portion 22d and the sheath 14 to adjust the longitudinal position of the balloon catheter 20.

In this form, the thin support rod 26 extends out of the second branch portion 22e for manipulation by the user. The thin support rod 26 can be pushed and pulled through the second branch portion 22e to adjust the longitudinal portion of the thin support rod 26 and the end of the helix 30 coupled thereto.

The thick support rod 24 can extend out of the proximal end 22c of the longitudinal portion 22a and be rotationally fixed to the spinner 28, which is rotationally coupled to the proximal end 22c of the longitudinal portion 22a of the handle 22. Thus, rotation of the spinner 28 will cause rotation of the thick support rod 24; however, the thick support road 24 can still be pushed or pulled through the spinner and the longitudinal portion 22a of the handle 22 to adjust the longitudinal position of the thick support rod 24 and the end of the helix 30 coupled thereto.

In one form, the proximal end 18a of the double lumen catheter 18 can be split so that the first lumen extends into the proximal end 22c of the handle 22, and the second lumen extends into the second branch 22e.

Of course, it will be appreciated that various configurations of the handle 22 could also be used, with the components extending out of the handle 22 through different handle portions, or the spinner 28 being coupled to a different branch to allow for rotation of a different component, if desired. The various combinations will be apparent to one skilled in the art without undue experimentation.

The system 10 is configured for being inserted into the patient's body in a first configuration, also known as a delivery configuration, which is shown in FIG. 1. In this configuration, the double lumen catheter 18, the retriever 16, and the balloon catheter 20 are each housed within the sheath 14. More specifically, the retriever 16 is partially housed within the double lumen catheter 18. The distal end 26b of the thin support rod 26 can be housed within the double lumen catheter 18 or it can extend a small amount from the double lumen catheter 18. The thick support rod 24 can extend out of the double lumen catheter 18 so that the distal end 24b of the thick support rod 24 extends distally past the distal end 26b of the thin support rod 26. The helix 30, which is coupled at one end to distal end 26b of the thin support rod 26 and at the other end to the distal end 24b of the thick support rod 24, will spiral and wrap around in a helical pattern around the balloon catheter 20. The balloon catheter 20 is in a deflated state, and extends along the support rods 24, 26 and through the helix 30. The distal end 20b and balloon portion 20c of the balloon catheter 20 can be disposed distally from the distal end of the thick support rod 24.

Once inserted into the patient's body, the system 10 can transition from the delivery configuration to other configurations related to retrieving the filter 12. The balloon catheter 20, double lumen catheter 18, and retriever 16 can be exposed from the sheath 14, as shown in FIG. 2. This exposure can occur as a result of the sheath 14 being retracted, or the components being translated distally out of the sheath 14. In either case, the components are moved distally relative to the sheath 14 to expose the components.

The thin support rod 26 can be moved distally relative to the thick support rod 24, such that the distal end 26b of the thin support rod 26 is moved toward the distal end 24b of the thick support rod 24. This relative movement of the distal ends 24b, 26b of the support rods 24, 26 toward each other will cause the helix 30 to compress longitudinally. The support rods 24, 26 can be generally fixed rotationally during their relative longitudinal translation. By holding the support rods 24, 26 rotationally fixed, the longitudinal compression of the helix 30 will cause the helix 30 to expand radially. Of course, the helix 30 will still expand radially even if the rods 24, 26 rotate slightly. Conversely, if the thin support rod 26 is refracted from this position, the helix 30 will elongate or stretch, causing the helix 30 to compress radially toward its delivery configuration size and shape. Thus, it will be appreciated that relative translation of the thin support rod 26 relative to the thick support rod can adjust the radial and longitudinal shape of the helix 30.

In addition to the adjustment of the helix 30 made possible by the longitudinal translation of the support rods 24 and 26 relative to each other, the shape of the helix 30 can be adjusted by rotating the thick support rod 24 while keeping the thin support rod 26 rotationally fixed. Adjusting the shape of the helix 30 is generally performed with the thin support rod 26 translated distally to expand the helix 30 radially, as described above. The longitudinally compressed and radially expanded shape of the helix 30 defines a slack portion 30a of the helix 30 that can be wound or unwound. In the case of the elongated and radially compressed helix shape 30, which exists in the delivery configuration or when the thin support rod 26 is retracted proximally from the thick support rod 24, there is relatively little slack as the helical winding is relatively tight around balloon catheter 20 (FIG. 1) relative to the radially expanded shape of the helix 30 (FIG. 2).

To wind the helix 30, the thick support rod 24 can be rotated in a first rotary direction via the spinner 28 at the handle 22, with the thin support rod 26 held relative fixed rotationally. Rotating the thick support rod 24 will cause the end of the helix 30 coupled thereto to wind along with the rotation of the thick support rod 24. Continued rotation of the thick support rod 24 will cause continued winding of the helix 30. By winding the helix 30, the helix 30 will become radially compressed, which can be used to compress or grasp an object that is disposed within the helix, such as the filter 12 (see FIG. 8). Conversely, the thick support rod 24 can be rotated in a second rotary direction that is opposite the first rotary direction to unwind the helix 30. Thus, the radial shape of the helix 30 can be adjusted by rotating the spinner 28 and thick support rod 24 back and forth.

It will be appreciated, however, that the rotation of the thick support rod 24 is performed relative to the thin support rod 26. The thin support rod 26 is preferably held rotationally fixed while the thick support rod 24 rotates. But the thin support rod 26 could also rotate in the same direction as the thick support rod, but rotate less, allowing the thick support rod 24 to wind the helix 30 at a slower rate relative to holding the thin support rod 26 fixed. Similarly, the thin support rod 26 could be rotated in the opposite direction of the thick support rod 24, increasing the rate of winding the helix 30. Thus, one skilled in the art will appreciate that references to rotating the thick support rod 24 to wind or unwind the helix 30 can likewise encompass any scenario where the thick support rod 24 rotates at a relative rate to the thin support rod 26.

Moreover, rotation of the thick support rod 24 relative to the thin support rod 26 is preferably performed with the support rods 24, 26 held longitudinally fixed. However, the winding or unwinding of the helix 30 caused by the rotation can be coupled with longitudinal translation of the support rods 24, 26 relative to each other. For example, as the helix 30 is being radially compressed by winding, the helix can simultaneously be elongated and radially compressed by proximally retracting the thin support rod 26. Similarly, the helix 30 can be radially compressed by rotation while being radially expanded by translating the thin support rod 26 distally relative to the thick support rod 24. Thus, a person having skill the art will appreciate that the helix 30 adjustment can be performed both by translating the rods 24, 26 relative to each other and/or rotating the rods 24, 26 relative to each other to achieve the desired shape adjustment.

The above description has referred to the thick support rod 24 as being the primary rotated component and the thin support rod 26 as the primary translating component to adjust the shape of the helix 30. However, it will be appreciated that the thick support rod 24 could be the primary translating component in addition to rotating, or the thin support rod could be the primary rotating component in addition to translating. Similarly, the thin support rod 26 could be the rotating component and the thick support rod 24 could be the translating component.

Figure 5:
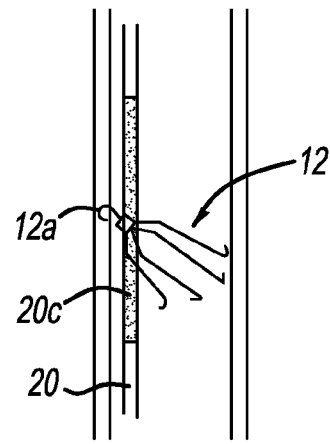
Figure 6:
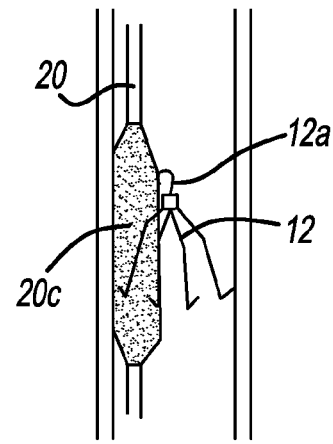
Figure 7:
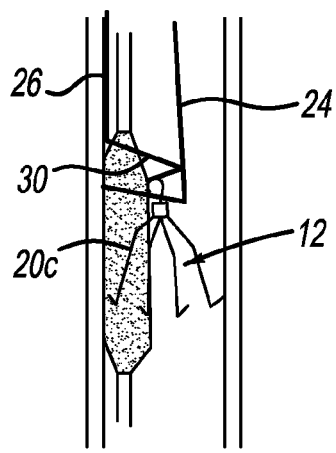
Figure 8:
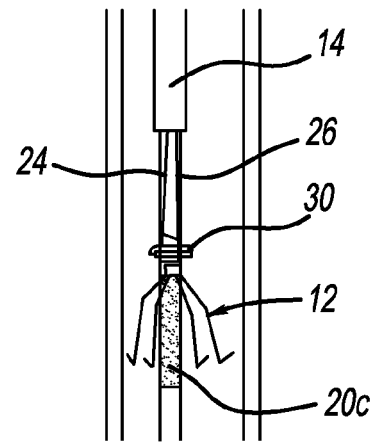

As previously described, the helix 30 wraps around the balloon catheter 20 in the delivery configuration shown in FIG. 1. In the exposed configurations, shown in FIGS. 2, 7, and 8, with the helix 30 radially expanded or compressed, the balloon catheter 20 can remain extended through the helix 30. The balloon portion 20c of the balloon catheter 20 is disposed preferably distally beyond the helix 30 in the delivery configuration shown in FIG. 1 and as initially deployed as shown in FIGS. 5 and 6. However, the balloon catheter 20 is longitudinally adjustable, and the balloon portion 20c can be adjusted and positioned within the helix 30 for being surrounded and compressed by the helix 30, as shown in FIGS. 7 and 8.

Having generally described the structure and function of the system 10 above, the use of the system 10 to retrieve the filter 12 from the patient's body will now be described.

With reference to FIGS. 4-9, the system 10 is provided in the delivery configuration with the sheath 14 housing the double lumen catheter 18, the balloon catheter 20, and the retriever 16 housed therein. The sheath 14 is inserted into the patient in a manner known in the art, such as via jugular artery access by using the Seldinger technique. Of course, other known methods could also be used. The sheath is advanced through the vasculature toward the location of the vena cava filter 12. The state of the system 10 as it is being delivered, and subsequently manipulated from the delivery state to retrieve the filter 12, can be monitored using known monitoring techniques.

Figure 4:
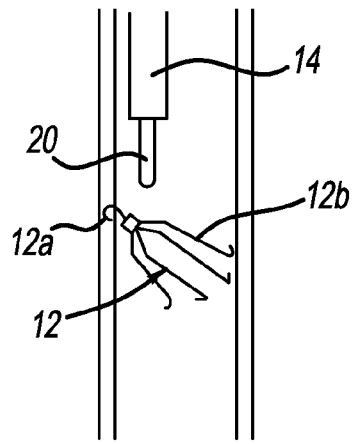
FIGS. 4-9 are schematic illustrations of the system in use to retrieve an implantable medical device from a patient blood vessel.

As shown in FIG. 4, the filter 12, having been delivered to the blood vessel previously, may have become tilted over time, causing a tip portion 12a of the filter to have become embedded in the vena cava wall. Additionally, struts 12b of the filter 12 may have also become embedded in the wall. The system 10 can be used to remove the tip 12a and the struts 12b from the vena cava wall so that the filter 12 can be retrieved.

With the system 10 delivered to the location of the filter 12, the filter 12 can be manipulated and retrieved by manipulating the system 10 according to the various above described functions.

As shown in FIG. 5, the balloon catheter 20 can be advanced distally out of the sheath 14 into the inferior vena cava (IVC) or other blood vessel where the filter 12 happens to be located. The balloon catheter 20 is then positioned between the IVC wall and the embedded tip 12a of the filter 12.

As shown in FIG. 6, the balloon catheter 20 is inflated using known methods, forcing the tip 12a away from the IVC wall. The inflation of the balloon catheter 20 can thereby remove the tip 12a from being embedded and can generally center the tip 12a of the filter 12 within the IVC.

This method of inflating the balloon catheter 20 can also be used to remove struts 12b that have become embedded in the IVC wall, or other portions of the filter 12 that have become embedded. The balloon catheter 20 can be deflated and repositioned to remove these other components, and this can be repeated until the filter 12 is sufficiently removed from its embedded condition.

The balloon catheter 20 has been described as forcing portions of the filter 12 away from the IVC wall to remove them from being embedded. In addition to this, the balloon catheter 20 can also operate to hold the filter 12 in place within the IVC after the filter 12 has been removed from its embedded condition.

With the tip 12a of the filter 12 no longer embedded in the IVC wall, the filter 12 can be generally oriented in a straight, or non-tilted, configuration, allowing for retrieval of the struts 12b and the remainder of the filter 12. The above description refers to retrieval of a filter with an embedded tip, but could also be used for filters that are not tilted or embedded.

The double lumen catheter 18, as well as the retriever 16 having the helix 30, is pushed distally to expose them from the sheath 14 and allow for retrieval of the filter 12. This exposed condition is shown in FIG. 2. This can be performed prior to inflating the balloon catheter 20, if desired, or after the balloon catheter 20 has been inflated to remove the embedded tip 12a from the IVC wall. Preferably, the distal end 18b of the double lumen catheter 18 is exposed from the sheath 14; however, the system 10 can still operate with the distal end 18b of the double lumen catheter 18 located proximal of the distal end 14b of the sheath 14.

The thin support rod 26 is pushed distally out of the double lumen catheter 18 and relative to the thick support rod 24, causing the helix 30 to expand radially. Of course, it will be appreciated that the helix 30 can be adjusted in shape using other methods of manipulating the thick support rod 24 and think support rod 26, as described previously above. The width of the helix 30 in the expanded condition generally depends on the overall length of the helix 30. The length of the helix 30 can be sized to accommodate various IVC sizes. In the event the helix 30 is sized to expand to a width that is wider than the width of the IVC, the expansion of the helix can be limited by adjusting the support rods 24, 26 as described to control the width of the expanded helix 30. For example, the average IVC diameter is approximately 15-25 mm. The helix 30 can be sized to have an outer diameter or width of approximately 12-15 mm to correspond to that size. Of course, these sizes are merely exemplary, and other sizes could also be used. The Nitinol construction of the helix 30 can help to assist the helix 30 expanding to the desired helical shape. Of course, the helix 30 could also be made from other shape memory materials or flexible formed wires to achieve the desired helical shape.

With reference to FIG. 7, the helix 30, in this expanded condition, can be advanced toward the filter 12 and the inflated balloon catheter 20. The helix 30 can be moved over the filter 12 and the balloon catheter 20. This can cause the tip 12a of the filter 12 to become trapped against the inflated balloon catheter 20.

With reference to FIG. 8, the helix 30 can then be radially compressed by rotating the thick support rod 24, as described above. Alternatively, other manners of radially compressing the helix 30 described above could also be used. As the helix 30 is radially compressed, the balloon catheter 20 can be deflated, as well. By deflating the balloon catheter 20 and tightening the helix 30 radially, the filter tip 12a and the filter 12 can become further trapped between the helix 30 and the balloon catheter 20. This deflation of the balloon catheter 20 and tightening of the helix 30 can continue until the balloon catheter 20 is substantially deflated and the helix is substantially tightened.

Figure 9:
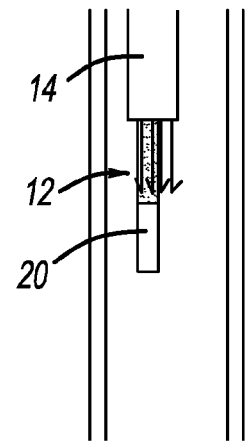

With reference to FIG. 9, with the filter 12 and balloon catheter 20 trapped within the helix 30, the sheath 14 can be advanced over the retriever 16, the balloon catheter 20, and the filter 12. With these components sheathed, the system 10 can be retracted from the patient's body using known methods. The sheathing action can be performed by advancing the sheath 14 over the components, or the components can each be retracted into the sheath 14. Thus, it will be appreciated that this movement is relative.

Thus, the above described system 10 and method provides an easy to use and robust solution for retrieving a filter from a body vessel, in particular a tilted filter within the IVC. The system 10 allows for the insertion of a single sheath having each of the components described above therein, such that additional tools and access sites into the patient's vasculature are generally unnecessary.

As a person skilled in the art will readily appreciate, the above description is meant as an illustration of implementation of the principles this invention. This description is not intended to limit the scope or application of this invention in that the invention is susceptible to modification, variation, and change, without departing from the spirit of this invention, as defined in the following claims.

What is claimed is:

1. A system for retrieving a medical device from a blood vessel, the system comprising:
    a balloon catheter having a proximal end and a distal end and an inflatable balloon portion disposed at the distal end;
    an elongate retrieval device extending along the balloon catheter, the retrieval device comprising a first elongate support rod having proximal and distal ends, a second elongate support rod having proximal and distal ends, and a helix extending between the distal ends of the first and second support rods, wherein the helix wraps circumferentially surrounding at least a portion of the balloon catheter;
    wherein the elongate retrieval device has a first condition, with the distal end of the second support rod being disposed proximally from the distal end of the first support rod, and the helix extending between the distal ends has a first width; and
    wherein the elongate retrieval device has a second condition, with the distal end of the second support rod being disposed distally relative to the first configuration and the helix extending between the distal ends of the first and second support rods has a second width that is greater than the first width.

2. The system of claim 1 further comprising a sheath that houses the balloon catheter and the elongate retrieval device in the first configuration, wherein the elongate retrieval device is translated distally relative to the sheath in the second configuration.

3. The system of claim 2 further comprising a double lumen catheter housed within the sheath in the first configuration, wherein the first and second support rods of the retrieval device extend through the double lumen catheter.

4. The system of claim 1, wherein the elongate retrieval device has a third condition, the first support rod in third second condition is rotated in a first direction relative to the first condition and the second condition, and the helix has a smaller width than the second condition.

5. The system of claim 2, further comprising a handle coupled to the proximal end of the sheath, wherein the first support rod, second support rod, and balloon catheter extend out of the handle.

6. The system of claim 5 further comprising a spinner rotatably coupled to the handle, wherein the first support rod is coupled to the spinner for rotation therewith.

7. The system of claim 1, wherein the helix is made from Nitinol, and has a width of approximately 12-15 mm in the second condition.

8. The system of claim 4, wherein the elongate retrieval device has a fourth condition, the first support rod is rotated in an opposite direction relative to the third condition, and the helix has a width that is larger than the third condition.

9. An apparatus for retrieving a medical device from a body vessel, the apparatus comprising: an elongate tubular sheath having a proximal end and a distal end and defining lumen extending therebetween; a double lumen catheter extending through the lumen of the sheath, the double lumen catheter having proximal and distal ends, a first lumen, and a second lumen; a balloon catheter extending through the lumen of the sheath alongside the double lumen catheter; a first support rod extending within the first lumen of the double lumen catheter; a second support rod extending within the second lumen of the double lumen catheter; and a helical member at least partially exposed from the double lumen catheter and extending between distal ends of the first and second support rods, wherein the size of the helical member is radially adjustable in response to rotation of the first support rod, wherein the helical member spirals around at least a portion of the balloon catheter.

10. The apparatus of claim 9, wherein the first support rod is thicker than the second support rod.

11. The apparatus of claim 9, wherein the first support rod is rotatable within the double lumen catheter.

12. The apparatus of claim 9, wherein the balloon catheter includes an inflatable balloon portion at a distal portion thereof, and the inflatable balloon portion is disposed distally from the distal end of the first support member.

13. The apparatus of claim 9, wherein the balloon catheter is longitudinally moveable relative to the helical member.

14. The apparatus of claim 12, wherein the helical member is longitudinally moveable to surround the inflatable balloon portion of the catheter and radially compressible to compress the inflatable balloon portion therein.

15. A method for retrieving an implantable medical device from a patient blood vessel, the method comprising:
    delivering a sheath having an inflatable balloon catheter and a radially adjustable retrieval device therein to a blood vessel, wherein the radially adjustable retrieval device includes a first support rod, a second support rod, and a helical member extending between distal ends thereof and surrounding a portion of the inflatable balloon catheter;
    translating the balloon catheter out of the sheath and between an implantable medical device and a wall of the blood vessel;
    inflating the balloon catheter against the wall of the blood vessel and against the implantable medical device and forcing the implantable medical device away from the blood vessel wall;

translating the helical member of the radially adjustable retrieval device at least partially over the balloon catheter and the implantable medical device;

radially compressing the helical member around the balloon catheter and the implantable medical device; and retracting the retrieval device, the balloon catheter and the implantable medical device.

16. The method of claim 15 further comprising translating the second support rod relative to the first support member to radially expand the helical member.

17. The method of claim 15 further comprising rotating the first support rod in a first rotary direction to radially compress the helical member.

18. The method of claim 15 further comprising translating the retrieval device, the balloon catheter, and the implantable medical device proximally into the delivery sheath.

19. The method of claim 16 further comprising translating the first support rod, the second support rod, and the helical member distally to surround at least a portion of an inflatable portion of the balloon and at least a portion of the implantable medical device.

\* \* \* \* \*